US011704793B2

(12) United States Patent
Ichinose et al.

(10) Patent No.: US 11,704,793 B2
(45) Date of Patent: Jul. 18, 2023

(54) DIAGNOSTIC SUPPORT SERVER DEVICE, TERMINAL DEVICE, DIAGNOSTIC SUPPORT SYSTEM, DIAGNOSTIC SUPPORT PROCESS,DIAGNOSTIC SUPPORT DEVICE, AND DIAGNOSTIC SUPPORT PROGRAM

(71) Applicants: FUJIFILM Corporation, Tokyo (JP); FUJIFILM Medical Systems USA, Inc., Lexington, MA (US)

(72) Inventors: Akimichi Ichinose, Tokyo (JP); Keigo Nakamura, Tokyo (JP); Noriaki Ida, Tokyo (JP); Keiji Sugihara, Tokyo (JP)

(73) Assignees: FUJIFILM Corporation, Tokyo (JP); FUJIFILM Medical Systems USA, Inc., Lexington, MA (US)

( * ) Notice: Subject to any disclaimer, the term of this patent is extended or adjusted under 35 U.S.C. 154(b) by 379 days.

(21) Appl. No.: 16/880,960

(22) Filed: May 21, 2020

(65) Prior Publication Data
US 2020/0286234 A1   Sep. 10, 2020

Related U.S. Application Data

(63) Continuation of application No. PCT/JP2018/038550, filed on Oct. 16, 2018.

(30) Foreign Application Priority Data

Nov. 24, 2017   (JP) ................ 2017-226149

(51) Int. Cl.
G06T 7/00       (2017.01)
G16H 50/20      (2018.01)
(Continued)

(52) U.S. Cl.
CPC ............ *G06T 7/0012* (2013.01); *A61B 8/463* (2013.01); *G16H 50/20* (2018.01); *H04N 7/157* (2013.01)

(58) Field of Classification Search
CPC ...... G06T 7/0012; G16H 50/20; A61B 8/463; H04N 7/157
See application file for complete search history.

(56) References Cited

U.S. PATENT DOCUMENTS

2006/0235716 A1   10/2006   Mahesh et al.
2012/0166546 A1    6/2012   Venon et al.

FOREIGN PATENT DOCUMENTS

JP    2002342346    11/2002
JP    2002344636    11/2002
(Continued)

OTHER PUBLICATIONS

IP.com Search Report dated Feb. 26, 2004 (and English machine translated) issued in Application No. JP-2004062709-A (Year: 2004).*
(Continued)

Primary Examiner — Vu Le
Assistant Examiner — Winta Gebreslassie
(74) Attorney, Agent, or Firm — JCIPRNET

(57) ABSTRACT

A virtual conference in relation to diagnostic object data is created. Messages posted to the virtual conference from terminal devices of users participating in the virtual conference are received, and the posted messages are sent to the other terminal devices beside the terminal devices of the users. Information relating to the diagnostic object data is generated, which information is obtained in accordance with analysis results of analyzing the posted messages. The information relating to the diagnostic object data is sent to the terminal devices.

15 Claims, 11 Drawing Sheets

(51) Int. Cl.
*A61B 8/00* (2006.01)
*H04N 7/15* (2006.01)

(56) References Cited

FOREIGN PATENT DOCUMENTS

| JP | 2003310592 | | 11/2003 |
|---|---|---|---|
| JP | 2004062709 | | 2/2004 |
| JP | 2005278991 A | * | 10/2005 |
| JP | 2007141245 | | 6/2007 |
| JP | 2011003158 | | 1/2011 |
| JP | 2012141979 | | 7/2012 |

OTHER PUBLICATIONS

IP.com Search Report dated Nov. 29, 2002 (and English machine translated) issued in Application No. JP-2002342346-A (Year: 2002).*
IP.com Search Report dated Oct. 13, 2057 (and English machine translated) issued in Application No. JP-2005278991-A (Year: 2005).*
IP.com Search Report dated Jun. 7, 2007 (and English machine translated) issued in Application No. JP-2007141245-A (Year: 2007).*
"Office Action of Japan Counterpart Application", dated Jun. 1, 2021, with English translation thereof, p. 1-p. 7.
"International Search Report (Form PCT/ISA/210) of PCT/JP2018/038550," dated Jan. 22, 2019, with English translation thereof, pp. 1-5.
"Written Opinion of the International Searching Authority (Form PCT/ISA/237) of PCT/JP2018/038550," dated Jan. 22, 2019, with English translation thereof, pp. 1-11.

* cited by examiner

DIAGNOSTIC SUPPORT SERVER DEVICE, TERMINAL DEVICE, DIAGNOSTIC SUPPORT SYSTEM, DIAGNOSTIC SUPPORT PROCESS,DIAGNOSTIC SUPPORT DEVICE, AND DIAGNOSTIC SUPPORT PROGRAM

CROSS-REFERENCE TO RELATED APPLICATIONS

This application is a continuation application of International Application No. PCT/JP2018/038550, filed on Oct. 16, 2018, which is incorporated herein by reference in its entirety. Further, this application claims priority from Japanese Patent Application No. 2017-0226149, filed on Nov. 24, 2017, the disclosure of which is incorporated by reference herein in its entirety.

BACKGROUND

Technical Field

The present disclosure relates to a diagnostic support server device, terminal device, diagnostic support system, diagnostic support process, diagnostic support device and diagnostic support program for supporting diagnosis in medical treatment.

Related Art

Modalities such as computed tomography (CT), magnetic resonance imaging (Mill) and so forth have become widely used, capturing examination images to enable accurate diagnostics in many hospitals. In recent years, picture archiving and communications systems (PACS) have been introduced. A PACS uses the Digital Imaging and COmmunication in Medicine (DICOM) standard to manage image data acquired from the respective modalities, enabling unified management of the different kinds of image data. Meanwhile, electronic health records are being adopted, enabling the preparation of diagnostic information for a patient at the same time as a summary of examination information of the patient is created.

With the progress of communication technology, remote image diagnostics support services are now being provided, using communication technologies to conduct diagnostics from distant locations. It has also become possible to carry out training on the operation of modalities from distant locations. In particular, operator training is necessary for imaging subjects in appropriate imaging conditions with CT or MM. However, it is necessary to use the actual modalities to carry out training. Therefore, an operator must relocate to a dedicated room in which a modality is equipped. Moreover, it is difficult to use actual equipment to conduct operations or testing during, for example, ordinary diagnostic times in a hospital. In addition, numbers of actual machines are limited and it may not be possible to immediately conduct operations or testing at any time. Accordingly, Japanese Patent Application Laid-Open (JP-A) No. 2003-310592 discloses a technique of an operator and an adviser using a communication tool such as a chat tool to train operation skills while communicating in real time.

In order to perform accurate diagnostics on captured images, a system for creating a diagnostic report while a number of doctors exchange case opinions is called for. In particular, creating a high-quality diagnostic report while more widely utilizing knowledge from the specialist fields of diagnosticians is useful for medical treatment.

However, when a number of doctors with specialist fields are in, for example, a number of different clinical departments within the same hospital, diagnosticians are often in distant locations and it may be difficult to immediately arrange a conference. It is desirable to obtain various kinds of information from a PACS while performing diagnostics. It is also desirable to create a radiology report that incorporates the results of case opinions. However, in addition to time for providing case opinions, it takes time to create a separate radiology report.

SUMMARY

Accordingly, to solve the problems described above, an object of the present disclosure is to provide a diagnostic support server device, a diagnostic support device, terminal device, diagnostic support system, diagnostic support process and diagnostic support program that are capable of implementing a case conference between plural doctors at separate locations.

A diagnostic support server device of the present disclosure includes: a message sending and receiving section that receives a message posted to a virtual conference from a terminal device of a user participating in the virtual conference and sends the posted message to another terminal device beside the terminal device of the user, the virtual conference being created in relation to diagnostic object data; an information generation section that generates information relating to the diagnostic object data, the information being obtained in accordance with an analysis result of analyzing the posted message; and a related information sending section that sends the information relating to the diagnostic object data to the terminal device of the user and the another terminal device.

A diagnostic support program of the present disclosure causes a computer to execute processing including: a message sending and receiving step of receiving a message posted to a virtual conference from a terminal device of a user participating in the virtual conference and sending the posted message to another terminal device beside the terminal device of the user, the virtual conference being created in relation to diagnostic object data; an information generation step of generating information relating to the diagnostic object data, the information being obtained in accordance with an analysis result of analyzing the posted message; and a related information sending step of sending the information relating to the diagnostic object data to the terminal device of the user and the another terminal device.

The meaning of the term "virtual conference" is intended to include messages and the like being exchanged and a conference being conducted electronically between plural users or between a user and a machine. For example, the term "virtual conference" may be used for chats, electronic conferencing, and systems such as electronic bulletin boards and the like.

The meaning of the term "information relating to diagnostic object data" may include images relating to diagnostic object data, may include information relating to a patient of the diagnostic object data, and may include data obtained by applying processing to diagnostic object data.

The diagnostic support server device may further include a summary generation section that generates a summary of messages posted to the virtual conference.

It is desirable if the summary is generated so as to include diagnosis information of the diagnostic object data.

The summary generation section may generate the summary when an end of diagnosis of the diagnostic object data in the virtual conference is detected.

The end of diagnosis may be detected at least one of when the posted message indicates the end of diagnosis or when a duration in which no message is posted to the virtual conference passes a predetermined duration.

It is desirable if the summary generation section associates the summary with the diagnostic object data and stores the summary and diagnostic object data at a storage section.

It is desirable if the information relating to the diagnostic object data includes at least one of an image in which image processing is applied to an image of the diagnostic object data, information that specifies a position of interest in an image of the diagnostic object data, an image in which a mark is applied to a position of interest in an image of the diagnostic object data, an image in which a position of interest in an image of the diagnostic object data is magnified, an image that is retrieved in relation to the diagnostic object data, information that specifies a slice position of a sectional image of the diagnostic object data, an image in which a density gradation of an image of the diagnostic object data is adjusted, and information that associates the posted message with an image that is an object.

The information relating to the diagnostic object data may be a key image used for a diagnosis of the diagnostic object data.

It is desirable if the summary generation section associates the key image with the summary and stores the key image and summary at a storage section.

A diagnostic support system of the present disclosure includes a diagnostic support server device and a plurality of terminal devices, the diagnostic support server device including: a message sending and receiving section that receives a message posted to a virtual conference from the terminal device of a user participating in the virtual conference and sends the posted message to another of the terminal devices beside the terminal device of the user, the virtual conference being created in relation to diagnostic object data; an information generation section that generates information relating to the diagnostic object data, the information being obtained in accordance with an analysis result of analyzing the posted message; and a related information sending section that sends the information relating to the diagnostic object data to the terminal device of the user and the another terminal device, and each terminal device including: a diagnostic object data display section that displays the diagnostic object data; a post message sending section that sends a message to be posted to the virtual conference to the diagnostic support server device; a virtual conference display section that displays the posted message in order of posting to the virtual conference; and a related information display section that displays the information relating to the diagnostic object data.

A diagnostic support process of the present disclosure is a diagnostic support process of a diagnostic support system including a diagnostic support server device and a terminal device, the diagnostic support process including: a message sending and receiving step of the diagnostic support server device receiving a message posted to a virtual conference from the terminal device of a user participating in the virtual conference and sending the posted message to another terminal device beside the terminal device, the virtual conference being created in relation to diagnostic object data; an information generation step of the diagnostic support server device generating information relating to the diagnostic object data, the information being obtained in accordance with an analysis result of analyzing the posted message; a related information sending step of the diagnostic support server device sending the information relating to the diagnostic object data to the terminal device and the another terminal device, a diagnostic object data display step of the terminal device displaying the diagnostic object data; a post message sending step of the terminal device sending a message to be posted to the virtual conference to the diagnostic support server device; a virtual conference display step of the terminal device displaying the posted message in order of posting to the virtual conference; and a related information display step of the terminal device displaying the information relating to the diagnostic object data.

A diagnostic support device of the present disclosure includes: a diagnostic object data display section that displays diagnostic object data; a post message acceptance section that accepts entry of a message to be posted to a virtual conference, the virtual conference being created in relation to the diagnostic object data; a virtual conference display section that displays the posted message in order of posting to the virtual conference; an information generation section that generates information relating to the diagnostic object data, the information being obtained in accordance with an analysis result of analyzing the posted message; and a related information display section that displays the information relating to the diagnostic object data.

Another diagnostic support process of the present disclosure includes: a diagnostic object data display step of displaying diagnostic object data; a post message acceptance step of accepting entry of a message to be posted to a virtual conference, the virtual conference being created in relation to the diagnostic object data; a virtual conference display step of displaying the posted message in order of posting to the virtual conference; an information generation step of generating information relating to the diagnostic object data, the information being obtained in accordance with an analysis result of analyzing the posted message; and a related information display step of displaying the information relating to the diagnostic object data.

Another diagnostic support program of the present disclosure causes a computer to execute processing including: a diagnostic object data display step of displaying diagnostic object data; a post message acceptance step of accepting entry of a message to be posted to a virtual conference, the virtual conference being created in relation to the diagnostic object data; a virtual conference display step of displaying the posted message in order of posting to the virtual conference; an information generation step of generating information relating to the diagnostic object data, the information being obtained in accordance with an analysis result of analyzing the posted message; and a related information display step of displaying the information relating to the diagnostic object data.

Another diagnostic support server device of the present disclosure includes a memory storing instructions executable by a computer and a processor configured to execute the stored instructions, the processor executing: a message sending and receiving step of receiving a message posted to a virtual conference from a terminal device of a user participating in the virtual conference and sending the posted message to another terminal device beside the terminal device of the user, the virtual conference being created in relation to diagnostic object data; an information generation step of generating information relating to the diagnostic object data, the information being obtained in accordance with an analysis result of analyzing the posted message; and a related information sending step of sending the information relating to the diagnostic object data to the terminal device of the user and the another terminal device.

Another diagnostic support device of the present disclosure includes a memory storing instructions executable by a computer and a processor configured to execute the stored instructions, the processor executing: a diagnostic object data display step of displaying diagnostic object data; an acceptance step of accepting entry of a message to be posted to a virtual conference, the virtual conference being created in relation to the diagnostic object data; a virtual conference display step of displaying the posted message in order of posting to the virtual conference; an information generation step of generating information relating to the diagnostic object data, the information being obtained in accordance with an analysis result of analyzing the posted message; and a related information display step of displaying the information relating to the diagnostic object data.

According to the present disclosure, a virtual conference is generated in relation to diagnostic object data, a message is posted to the virtual conference from a terminal device of a user participating in the virtual conference and, in accordance with analysis results of analyzing the posted message, information relating to the diagnostic object data is generated and sent to the terminal device. Therefore, messages posted to the virtual conference and information relating to the diagnostic object data in response to messages may be generated automatically and may be reviewed at terminal devices connected by a network. Thus, a conference about a case may be conducted between doctors at separate locations.

DETAILED DESCRIPTION

Figure 1:
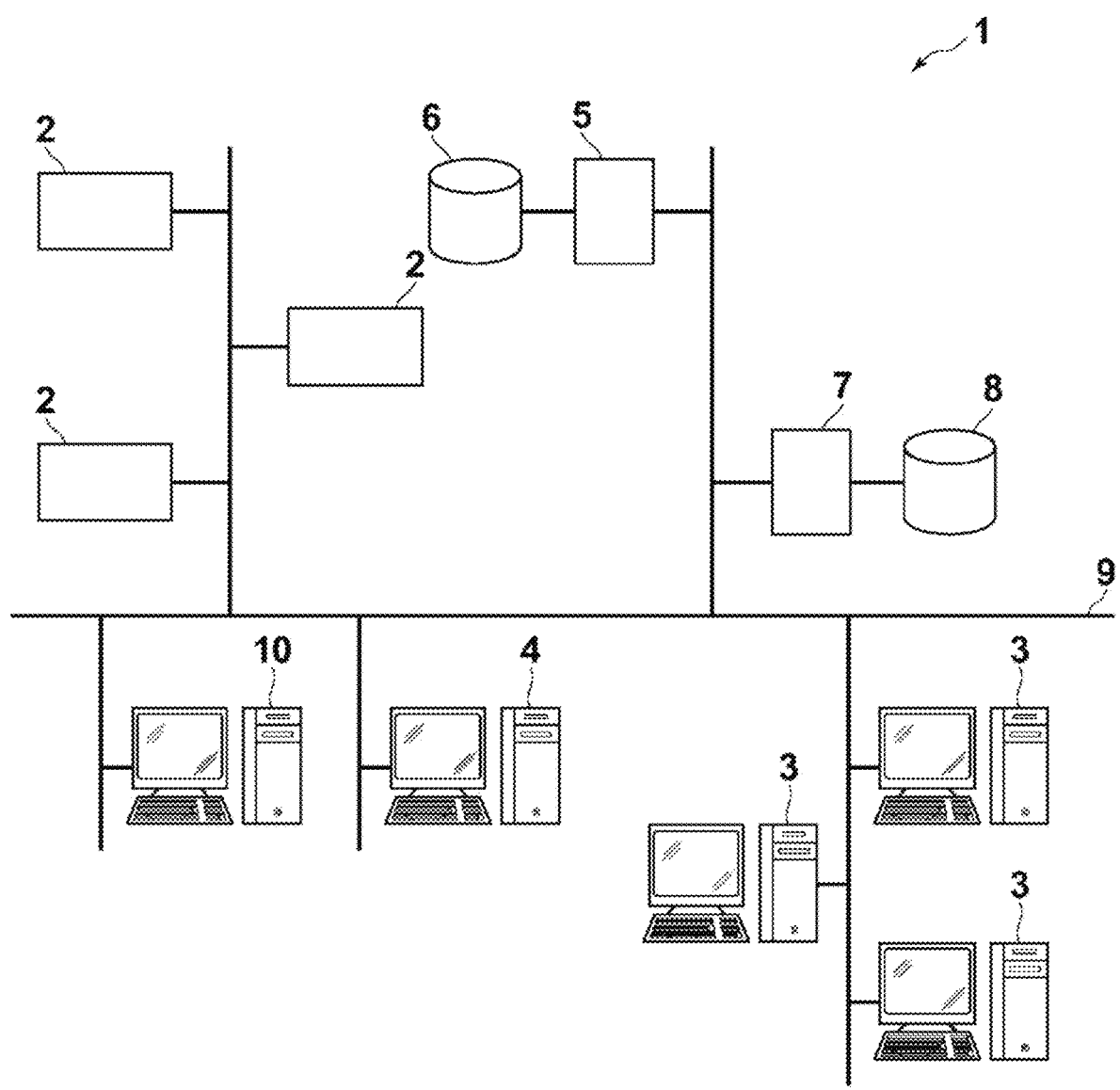
FIG. 1 is a diagram showing a schematic configuration of a medical information system.

Below, a diagnostic support system according to a first exemplary embodiment of the present disclosure is described with reference to the drawings. FIG. 1 is a block diagram showing a schematic configuration of a medical information system that is provided with the diagnostic support system according to the present exemplary embodiment.

A medical information system 1 shown in FIG. 1 is a system for implementing, in response to examination requests from doctors in clinical departments using a publicly known ordering system: imaging of examination target areas of imaging subjects; management of medical images acquired by imaging; interpretation of medical images by radiologists and the creation of radiology reports; viewing of the radiology reports by doctors in the clinical departments that made the requests; and detailed examination of medical images of radiology objects. As shown in FIG. 1, the medical information system 1 is configured with plural modalities (imaging devices) 2, plural radiology workstations 3 (below referred to as "the radiology WS 3") that are terminal devices, a clinical department workstation 4 (below referred to as "the clinical department WS 4"), an image server 5, an image database 6, a radiology report server 7, a radiology report database 8, and a diagnostic support server device 10 according to the present exemplary embodiment, which are connected to one another via a network 9 in a state in which communications are possible.

Each device is a computer at which an application program is installed that causes the computer to function as a structural element of the medical information system 1. The application program is recorded and distributed on a storage medium such as a DVD (Digital Versatile Disc), a CD-ROM (Compact Disc Read-Only Memory) or the like, and is installed from the recording medium onto the computer. Alternatively, the application program is stored in a storage device of a server computer or in network storage connected to the network, in a state that is accessible from elsewhere, and is downloaded onto the computer and installed when requested.

Each modality 2 is a device that, by imaging an area that is a diagnostic object of an imaging subject, creates a medical image representing the diagnostic object area. More specifically, the modalities 2 are a CT device, an MRI device, a computed radiography (CR) device, an ultrasound device and the like. Imaged three-dimensional volume data is sent over the network 9 to the image server 5 and saved in accordance with storage formats conforming to the DICOM (Digital Imaging and COmmunication in Medicine) standard and with communications standards.

The radiology workstation 3 is a computer that a medical imaging radiologist uses for interpreting the medical images and creating radiology reports. The radiology workstation 3 is structured with a processor, a high-resolution display, and input devices such as a keyboard and mouse or the like. The radiology workstation 3 implements processes such as medical image viewing requests to the image server 5, various kinds of image processing of medical images received from the image server 5, display of the medical images, support for the creation of radiology reports, radiology report recording requests and viewing requests to the radiology report server 7, display of radiology reports received from the radiology report server 7, and so forth. The processes are implemented by the radiology workstation 3 executing a software program for each process. Rather than each process being executed at the radiology workstation 3, a separate image processing server may be connected to the network 9 and processes may be executed by the image processing server in response to processing requests from the radiology workstation 3.

The clinical department workstation 4 is a computer that a doctor in a clinical department uses for detailed examination of images, viewing of radiology reports, creation of electronic health records and so forth. The clinical department workstation 4 is structured with a processor, a high-resolution display, and input devices such as a keyboard and mouse or the like. The clinical department workstation 4 implements processes such as image viewing requests to the image server 5, display of images received from the image server 5, automatic detection or enhanced display of apparently lesion areas, radiology report viewing requests to the radiology report server 7, display of radiology reports received from the radiology report server 7, and so forth. The processes are implemented by the clinical department workstation 4 executing a software program for each process.

The image server 5 is a general purpose computer with relatively high processing capability on which a software program that provides the functions of a database management system (DBMS) is installed. The image server 5 is provided with large-capacity storage constituting the image database 6. This storage may be a large-capacity hard disc device that is connected to the image server 5 by a data bus, or may be network attached storage (NAS) connected to the network 9 and a disc device connected to a storage area network (SAN). When the image server 5 receives medical image recording requests from the modalities 2, the image server 5 puts the medical images into a database format and records the medical images in the image database 6.

The image database 6 records image data of medical images acquired by the modalities 2 and supplementary information. The supplementary information may include information such as, for example: an image ID (identification) for identifying an individual medical image; a patient ID for identifying the imaging subject; an examination ID for identifying the examination; a unique identification (UID) assigned to each individual medical image; an examination date and examination time when the medical image was created; the type of modality used in the examination for acquiring the medical image; patient information such as the patient's name, age, sex and so forth; the examined area (imaged area); imaging information (an imaging protocol, imaging sequence, imaging method, imaging conditions, use of a contrast agent and so forth); a series number or sample number when plural medical images are acquired in a single examination; and the like.

When the image server 5 receives a viewing request from the radiology workstations 3 through the network 9, the image server 5 retrieves a medical image recorded in the image database 6 and sends the extracted medical image to the radiology workstation 3 that was the source of the request.

The radiology report server 7 is a general purpose computer in which a software program that provides the functions of a database management system (DBMS) is embedded. When the radiology report server 7 receives radiology report recording requests from the radiology workstations 3, the radiology report server 7 puts the radiology reports into a database format and records the radiology reports in the radiology report database 8.

The radiology report database 8 records radiology reports storing information such as, for example, an image ID identifying a medical image of a radiology object, a radiologist ID for identifying an image diagnostician interpreting the image, a lesion name, location information of the lesion, a finding, a confidence level of the finding, and the like.

The network 9 is a wired or wireless local area network connecting various kinds of equipment in a hospital. If any of the radiology workstations 3 are located in another hospital or clinic, the network 9 may connect respective local area networks of the hospitals to one another through the Internet or a dedicated circuit. In any case, it is preferable if the network 9 is configured to be capable of implementing high-speed transfers of medical images, such as an optical network or the like.

The diagnostic support system of the present disclosure is constituted by the diagnostic support server device (below referred to as "the diagnostic support server") 10 and terminal devices.

The diagnostic support server 10 is a general purpose computer provided with widely known hardware structures such as a central processing unit (CPU) 11, memory (a main storage device) 12, storage (an auxiliary storage device) 13, an input/output interface (not shown in the drawings), a communications interface 14, a database (not shown in the drawings) and the like. In addition to a widely known operating system, server software and the like is installed on the diagnostic support server 10. The storage 13 is structured with a hard disk, solid state drive (SSD) or the like. As required, the computer may be provided with a graphics processing unit (GPU).

A diagnostic support program may be stored, in a state that is accessible from elsewhere, in a storage device of a computer connected to the network or in network storage and may, in response to requests from elsewhere, be downloaded to computers and installed. Alternatively, the diagnostic support program is recorded and distributed on a storage medium such as a DVD, a CD-ROM or the like, and is installed from the storage medium onto a computer.

During operations of this computer, the diagnostic storage program is stored in the memory 12, and the CPU 11 executes processing in accordance with the program stored in the memory 12. Thus, the computer functions as the diagnostic support server. In the present exemplary embodiment, the CPU 11 executes the functions of respective sections of the diagnostic support server in accordance with the diagnostic support program. However, as an alternative to the CPU 11 that is a general purpose processor that executes software to function as various processing sections, a programmable logic device (PLD) may be employed. The PLD is a processor whose circuit structure may be altered after fabrication, such as a field programmable gate array (FPGA) or the like. Alternatively, the processing of each section may be executed by a dedicated electronic circuit or the like, which is a processor with a circuit structure specifically designed to execute dedicated processing, such as an application-specific integrated circuit (ASIC) or the like.

A single processing section may be structured by one of these various kinds of processors, or may be structured by combining two or more processors of the same or different kinds (for example, plural FPGAs, a combination of a CPU and an FPGA, or the like). Furthermore, plural processing sections may be structured by a single processor. As an example of a structure in which plural processing sections are structured by a single processor, in a first mode, a single processor is structured by a combination of one or more CPUs and software, as typified by client and server computers or the like, and the processor functions as the plural processing sections. In a second mode, a processor that realizes the functions of a whole system including plural processing sections with a single integrated circuit (IC) is employed, as typified by a system-on-chip (SoC) or the like.

Thus, the various processing sections are configured using one or more of the various kinds of processor described above as hardware structures.

In the present exemplary embodiment, a terminal program of the diagnostic support system of the present disclosure is installed at the clinical department workstation 4 and radiology workstations 3, causing the clinical department workstation 4 and radiology workstations 3 to function as terminal devices.

Figure 2:
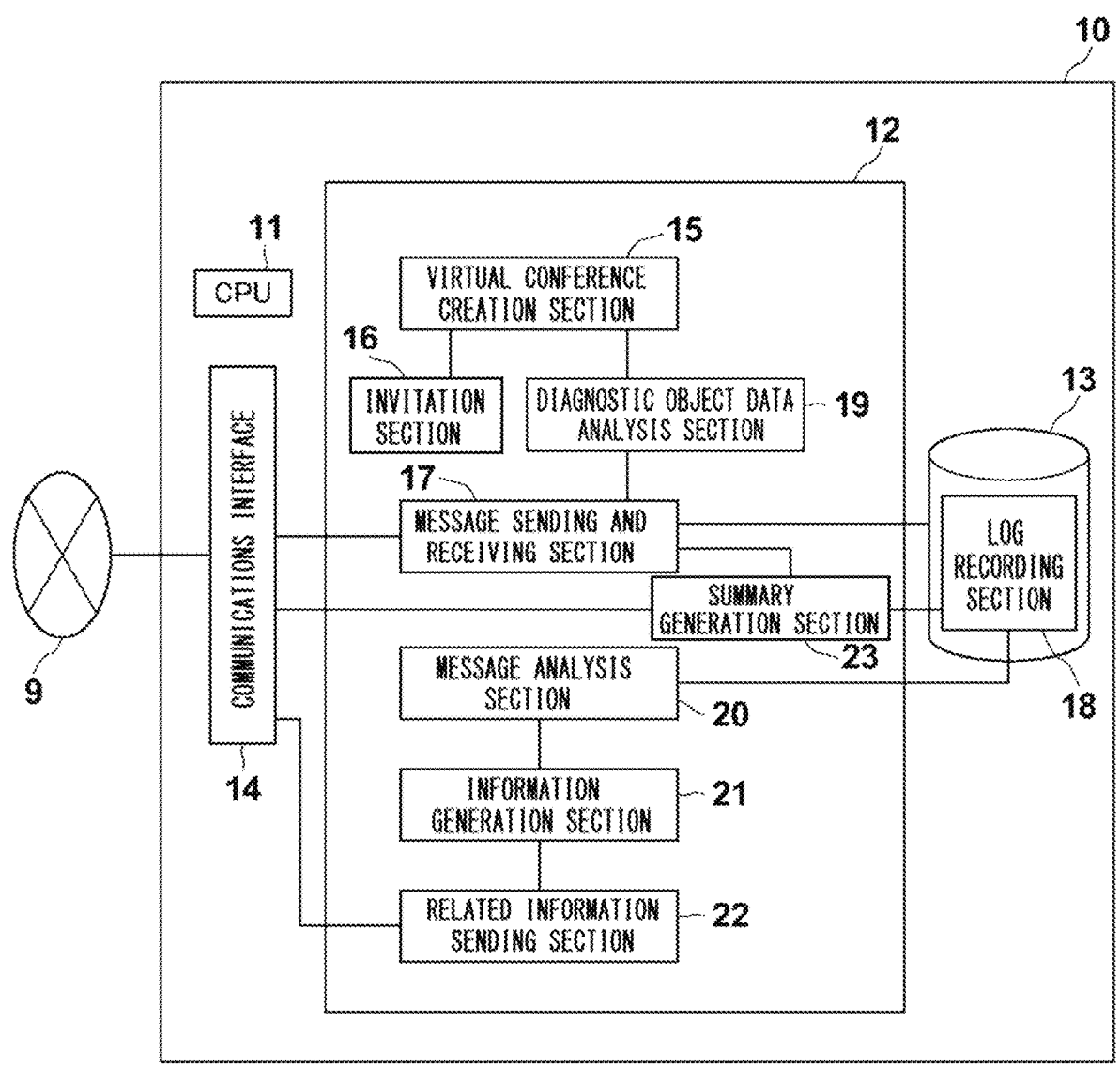
FIG. 2 is a diagram showing a schematic configuration of a diagnostic support server device according to a first exemplary embodiment of the present disclosure.

Now, functions of the diagnostic support server 10 according to the first exemplary embodiment are described. As shown in FIG. 2, the diagnostic support server 10 according to the first exemplary embodiment functions as a virtual conference creation section 15, an invitation section 16, a message sending and receiving section 17, a log recording section 18, a diagnostic object data analysis section 19, a message analysis section 20, an information generation section 21, a related information sending section 22, and a summary generation section 23.

When the diagnostic support server 10 receives diagnostic object data, the virtual conference creation section 15 automatically creates a virtual conference. It is sufficient that the virtual conference enables plural users to exchange messages. For example, the virtual conference may be implemented using a chat tool, electronic conferencing, or the functions of a bulletin board or the like. In the present exemplary embodiment below, a virtual conference that employs chat functions is described as an example.

The diagnostic object data may be a medical image captured by the modalities 2, or may be an electrocardiogram, the results of a blood test or the like. In the present exemplary embodiment below, a case in which the diagnostic object data is a medical image for examining a disorder of a patient (below referred to as a scan image) is described as an example.

The log recording section 18 is a region in the storage 13 that is assigned to a single virtual conference. The log recording section 18 records messages posted to the virtual conference in the order they are posted.

The invitation section 16 sends messages to the terminal devices inviting users to participate in the virtual conference. If the virtual conference is created as a thread in a chat tool, the invitation section 16 generates messages for inviting doctors suitable for diagnosis of the diagnostic object data (diagnosticians, radiology specialists and the like), and sends the messages to the terminal devices with corresponding user accounts. The invited users may be doctors registered manually by the user who recorded the diagnostic object data, or doctors associated with the case may be registered beforehand and invited automatically. When, for example, a user is a diagnostician, the terminal device is the clinical department workstation 4 of the corresponding clinical department, and when a user is a radiologist, the terminal device is one of the radiology workstations 3. When a notification that a user has accepted the invitation message is received from the terminal device, the user can start sending and receiving messages in the virtual conference.

When the message sending and receiving section 17 receives a message posted to the virtual conference from the terminal device of a user, the message sending and receiving section 17 sends the posted messages to the terminal devices beside that of the user who posted the message. The messages are not limited to text; posted images may also be sent and received as messages.

When the virtual conference is created for a scan image, the diagnostic object data analysis section 19 automatically executes image analysis, such as identifying organs corresponding to the imaged area, identifying lesions and the like, and the diagnostic object data analysis section 19 posts the results of this analysis to the virtual conference. For example, in a case in which the scan image is a brain image, the diagnostic object data analysis section 19 posts a message to the virtual conference presenting analysis results of, for example, a bleeding position in the brain, a bleeding amount and the like; for example, "35 mL bleed observed in the left cerebellum." The diagnostic object data analysis section 19 may also post the scan image that is the diagnostic object of the virtual conference. Furthermore, depending on analysis results, the diagnostic object data analysis section 19 may post an image in which a mark is applied to a bleeding position or the like in the scan image to the virtual conference.

The message analysis section 20 performs analysis processing, such as natural language analysis or the like, on units of the messages posted from the terminal devices. It is sufficient that the message analysis results can provide information that clarifies what kind of processing should be executed in response to the messages. For example, the diagnostic support server 10 may obtain as analysis results: information that should be provided in response to the posted messages; information indicating that a posted message is a message to another user participating in the virtual conference; information indicating that a posted message is ending the virtual conference; and so forth.

For example, in a case in which the diagnostic object scan image that is the object of the conference is a CT image of a brain scan and bleeding is observed in the brain, then when a posted message is, for example, "What's the maximum diameter?", the analysis result obtained by the natural language analysis is that an image analysis to acquire a maximum diameter of the bleeding location is required. Alternatively, in a case in which a posted message is "What do you think, Jeff?", then if "Jeff" is a user participating in the virtual conference, an analysis result that this is a message to another user is obtained.

It is more preferable if the message analysis section 20 does not analyze each posted message as a unit but performs analysis taking into account previous messages according to the log of messages recorded in the log recording section 18.

The information generation section 21 generates information relating to the scan image in response to analysis results from the message analysis section 20. This information relating to the scan image may be an image relating to the scan image, may be information relating to the patient in the scan image, and may be an image or data obtained by applying processing to the scan image.

In the aforementioned example of a brain image, for example, when the message "What's the maximum diameter?" is posted, image analysis is applied to the CT scan image to acquire the maximum diameter of the bleeding location, and the result that is obtained (for example, a maximum diameter of 3.8 cm) is generated as the information relating to the scan image.

Further, the information relating to the scan image may be information that specifies a position of interest in the scan image. For example, when the scan image is a brain image, the information generation section 21 performs image analysis of the scan image, identifies an abnormal region such as a hemorrhage region, an infarction region or the like, and acquires a coordinate position of the abnormal region in the scan image. Alternatively, the information generation section 21 may acquire a region of the brain that is a location in which the region of interest is located as the position of interest; for example, the left cerebellum, the right cerebellum or the like. If the scan image is a thorax image or the like, an ischemic region of the heart may be identified as the abnormal region, and a position of this abnormal region acquired as the position of interest.

The information relating to the scan image may be an image in which a mark is applied to a position of interest in the scan image. When the scan image is a brain image as described above, the information generation section 21 may identify an abnormal region such as a hemorrhage region, an infarction region or the like, and create an image in which a mark is applied to clarify the abnormal region. For example, the abnormal region may be indicated by an arrow or the abnormal region may be encircled by a line. Alternatively, when the scan image is of the abdomen or the thorax, an organ may be identified as a region of interest and an image generated in which a mark is applied so as to clarify the organ region.

An image relating to the scan image may be an image in which a position of interest in the scan image is magnified. For example, if the message "Zoom in" is posted, in accordance with the analysis results analyzed by the message analysis section 20, the information generation section 21 extracts an abnormal region or organ region as described above to be the region of interest, and a magnified image is generated with the identified region as the position of interest.

The information relating to the scan image may be an image retrieved from the image server 5 that is an image relating to the scan image. Patient IDs conforming to the DICOM format are applied to examination images. Hence, the information generation section 21 may use a patient ID to retrieve other examination images of the same patient. For example, in many cases of diagnosing a brain disorder, both CT images and Mill images are captured. When CT images are being discussed in a virtual conference and, for example, the message "Show other images" is posted, in accordance with the analysis results analyzed by the message analysis section 20, Mill images may be retrieved.

The information relating to the scan image when the scan image is a CT image or an MM image may be information that specifies the slice position of a sectional image. The information generation section 21 may acquire the slice position in response to a message. A sectional image that is displayed at the start of a virtual conference may be switched to sectional images at different positions during the conference.

The information relating to the scan image may be an image in which image processing is applied to the scan image to adjust density gradations. Depending on imaging conditions of the modality, the appearance of light and shade may differ even when the same imaging subject is imaged. Further, there are cases in which diagnosis may be facilitated by an adjustment of density gradations. For example, when the message "Make the image sharper" is posted, in response to the analysis results analyzed by the message analysis section 20, the information generation section 21 may generate an image that is adjusted to a density gradation more suitable for the imaging conditions or the disorder.

The information relating to the scan image may be information that associates a message posted to the virtual conference with the image that is the object. For example, if the message "Show the first image" is posted, in response to the analysis results analyzed by the message analysis section 20, the information generation section 21 may retrieve the original diagnostic object scan image from the image server 5 and generate a message linking to a save location of this scan image.

The information relating to the diagnostic object data may be a key image used for a diagnosis of the scan image. On the basis of analysis results of messages posted to the virtual conference, the information generation section 21 specifies an image that is decisive for diagnosis from among images discussed by the virtual conference to be the key image. In a case in which the scan image is a CT image or an Mill image, the scan image includes plural sectional images, of which a single sectional image may be specified as the key image.

The related information sending section 22 sends the information relating to the scan image to the terminal devices of the users participating in the virtual conference. More specifically, the related information sending section 22 posts the information relating to the scan image to the virtual conference and sends the information to the terminal devices. Alternatively, when the information relating to the scan image is an image, the related information sending section 22 may send the image to viewers at the terminal devices, which viewers are separate from the virtual conference.

The summary generation section 23 generates a summary of messages posted to the virtual conference. The summary generation section 23 divides the messages into sentences, analyzes the sentences, assigns scores to the sentences, and determines the main points of the sentences. In particular, a widely known technique for creating summaries (for example, see JP-A No. 2011-003158) may be employed, such as assigning higher scores to sentences containing terms relating to diagnostic information that are used in the messages and to sentences containing terms that occur frequently, and creating the summary from sentences with high scores. In particular, by giving sentences containing terms relating to diagnostic information high scores and, among those terms, giving higher scores to the terms that occur more frequently, a summary may be automatically generated such that diagnostic information about the scan image is included.

The summary generation section 23 generates the summary when the end of diagnosis of the diagnostic object data in the virtual conference is detected. More specifically, the summary generation section 23 generates the summary when the analysis results of analyzing a posted message by the message analysis section 20 indicate the end of the diagnosis. Alternatively, the summary generation section 23 generates the summary when a duration in which no messages are posted to the virtual conference has passed a predetermined duration. The summary generation section 23 posts the generated summary to the virtual conference through the message sending and receiving section 17, as a result of which the summary is sent to the terminal devices.

The summary generation section 23 sends the generated summary and information of the scan image to the radiology report server 7, puts the summary and scan image into a report format, and stores this report in the radiology report database 8 (a storage section). Thus, radiology reports may be generated automatically from the messages posted to the virtual conference. Alternatively, the generated summary and scan image may be associated and stored in an electronic health record.

It is even more desirable if the summary generation section 23 associates the summary with the aforementioned key image that is decisive in the diagnosis, and stores the key image and summary in the radiology report database 8. This enables confirmation of which image was decisive in the diagnosis, which may contribute to appropriate treatment.

To perform image analysis of a scan image, the diagnostic support server 10 may be provided with a convolutional neural network (CNN) that employs a deep learning technique to conduct learning, and the CNN may be used for image analysis at the diagnostic object data analysis section 19 and the information generation section 21. It is desirable if the CNN of the present exemplary embodiment is configured to output an organ area or lesion area in a scan image when the scan image is inputted. Alternatively, a CNN that outputs a disorder name when a scan image is inputted may be provided, or a CNN that outputs a probability that the pixels in an image show a particular disorder among a number of disorders. Further, if a CNN that provides a number of these different results is provided, various image analyses may be performed.

A CNN that performs image analysis may be provided at an image processing server that is separately provided for image processing rather than at the diagnostic support server 10. Analysis of a scan image may be requested via the network, and only analysis results received.

Figure 3:
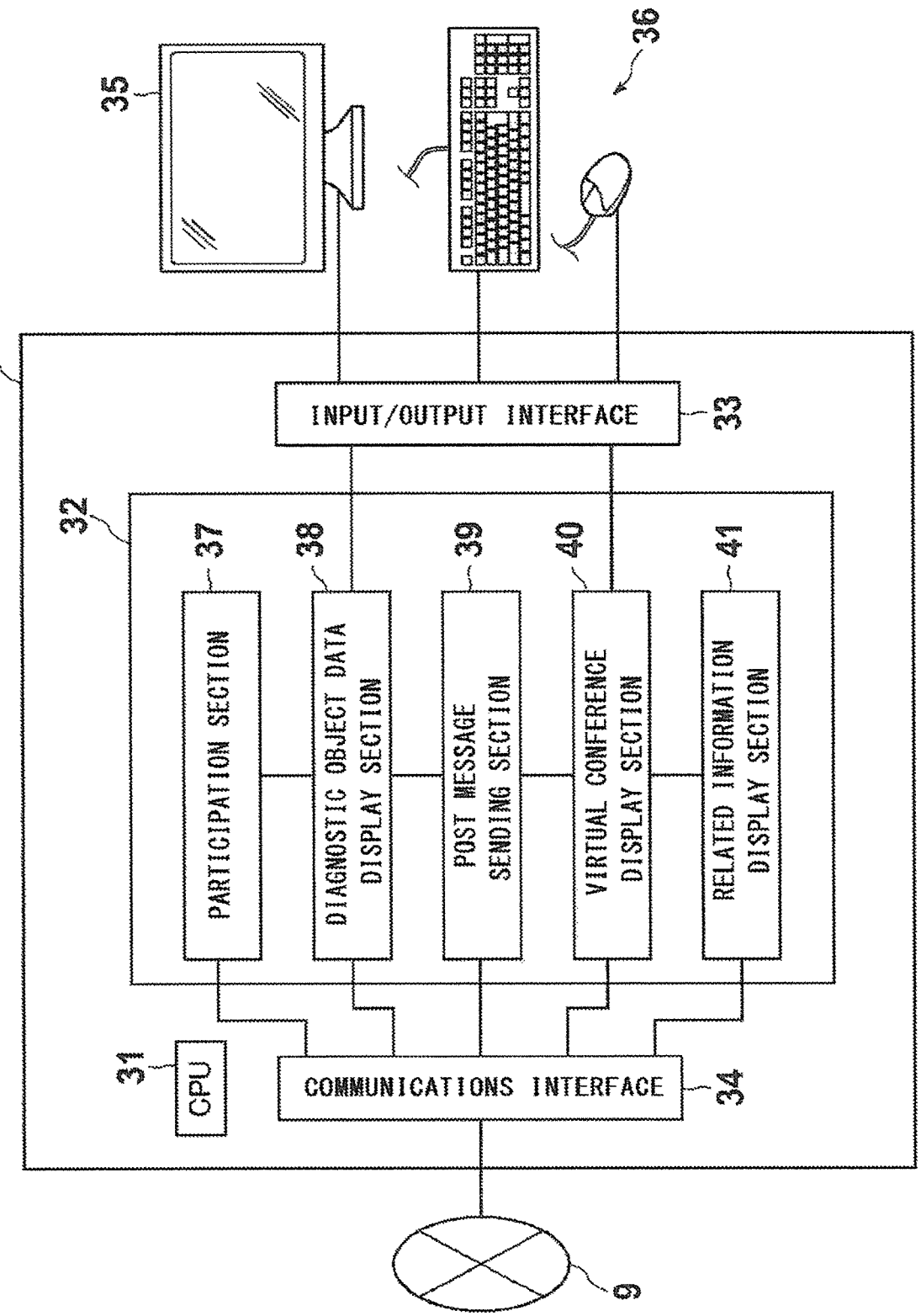
FIG. 3 is a diagram showing a schematic configuration of a terminal device according to the first exemplary embodiment of the present disclosure.

Now, configuration of a terminal device 30 according to the first exemplary embodiment is described. As shown in FIG. 3, the terminal device 30 is a computer equipped with widely known hardware structures such as a CPU 31, memory 32, storage (not shown in the drawings), an input/output interface 33, a communications interface 34, a data bus (not shown in the drawings) and the like. The terminal device 30 is connected to a display 35 and an input device 36 such as a keyboard and mouse or the like. During operations of this computer, a terminal device program is stored in the memory 32, and the CPU 31 executes processing in accordance with the program stored in the memory 32. Thus, the computer functions as the terminal device 30.

As shown in FIG. 3, the terminal device 30 functions as a participation section 37, a diagnostic object data display section 38, a post message sending section 39, a virtual conference display section 40 and a related information display section 41.

After the participation section 37 receives an invitation message from the diagnostic support server 10, the participation section 37 sends a notification of acceptance to the diagnostic support server 10. After acceptance is notified, messages may be posted to the virtual conference.

The post message sending section 39 sends post messages entered using the input device 36 to the diagnostic support server 10.

The virtual conference display section 40 displays messages posted to a thread at the display 24 in order of posting to the virtual conference. The virtual conference display section 40 receives messages posted by other users participating in the virtual conference, and messages posted by the diagnostic support server 10, from the diagnostic support server 10. The virtual conference display section 40 displays the received messages, and messages received by the diagnostic support server 10 from that terminal device through the post message sending section 39, in order of posting to the virtual conference.

The diagnostic object data display section 38 displays a scan image posted to the virtual conference from the diagnostic support server 10 at the display 35. Alternatively, the diagnostic object data display section 38 uses software for a viewer that is different from a window showing the thread of the virtual conference to display the scan image at the display 35.

The related information display section 41 displays information relating to the scan image that is posted to the virtual conference from the diagnostic support server 10. When the information relating to the scan image is posted to the thread of the virtual conference, the information relating to the scan image is displayed in the window of the thread of the virtual conference. Alternatively, in a case in which the information relating to the scan image is an image, the image may be displayed using the viewer.

Figure 4A:
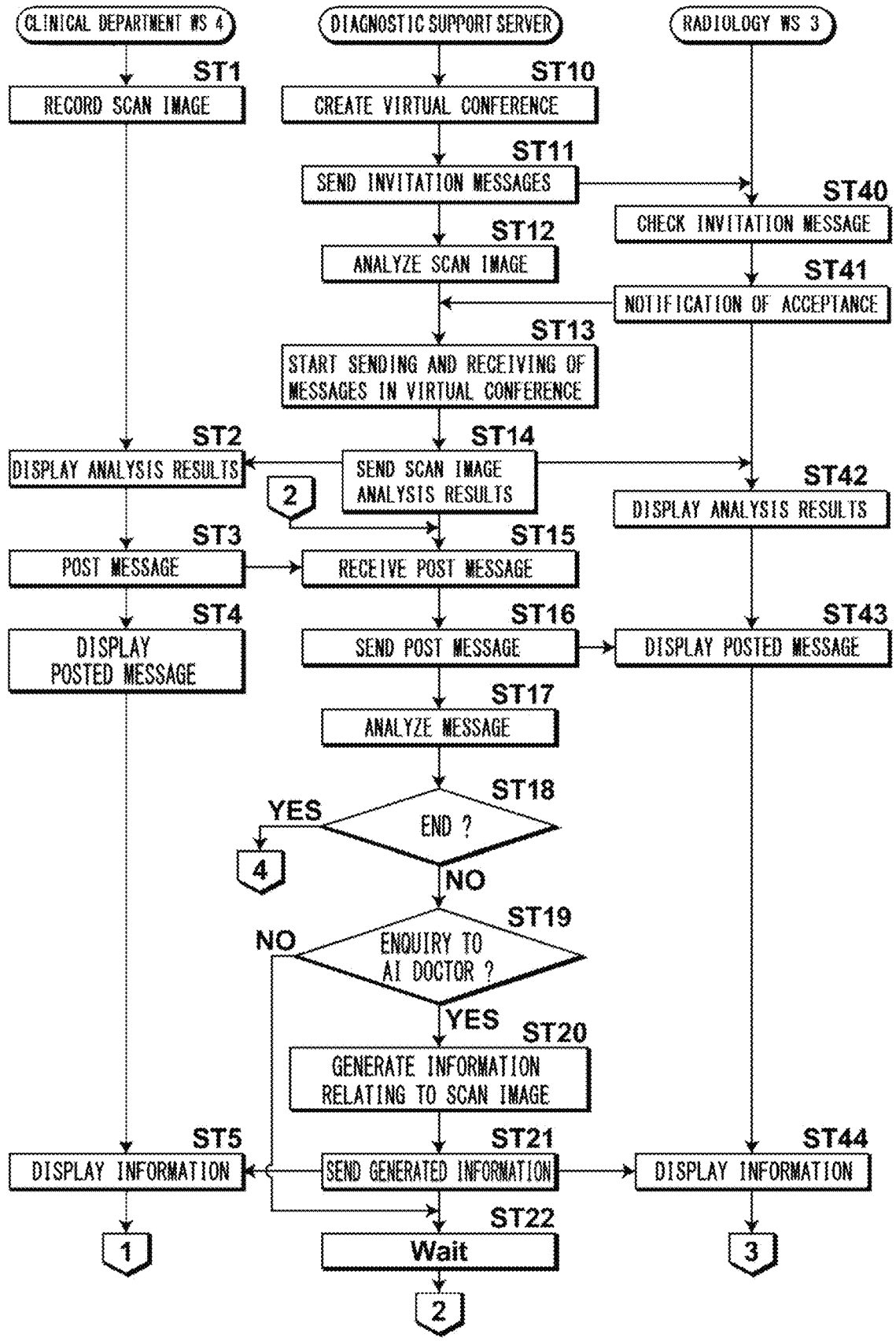
FIG. 4A is (part 1 of) a flowchart showing a flow of processing of a virtual conference according to the first exemplary embodiment of the present disclosure.
Figure 5:
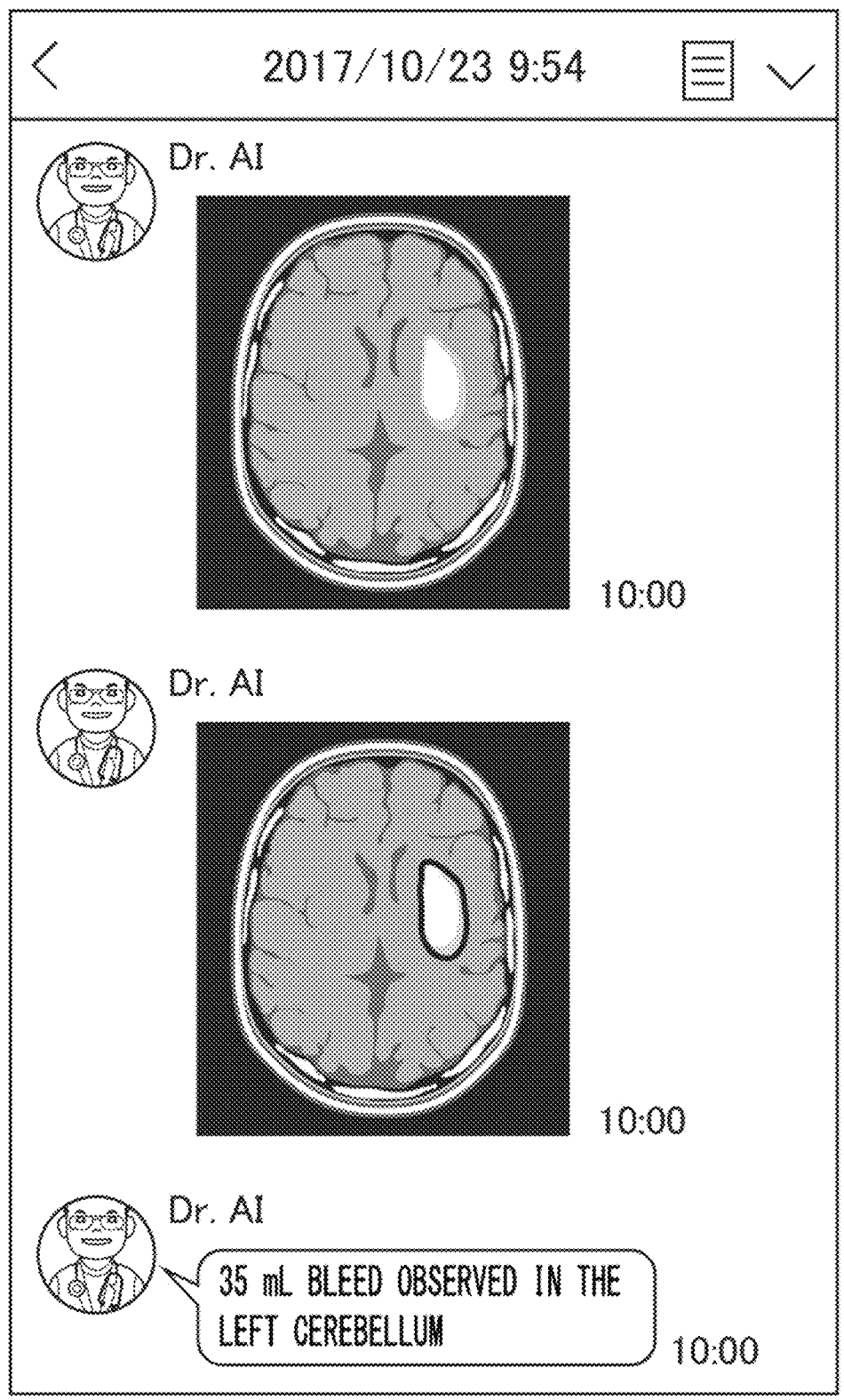
FIG. 5 shows an example of a display screen at the start of a virtual conference.
Figure 6:
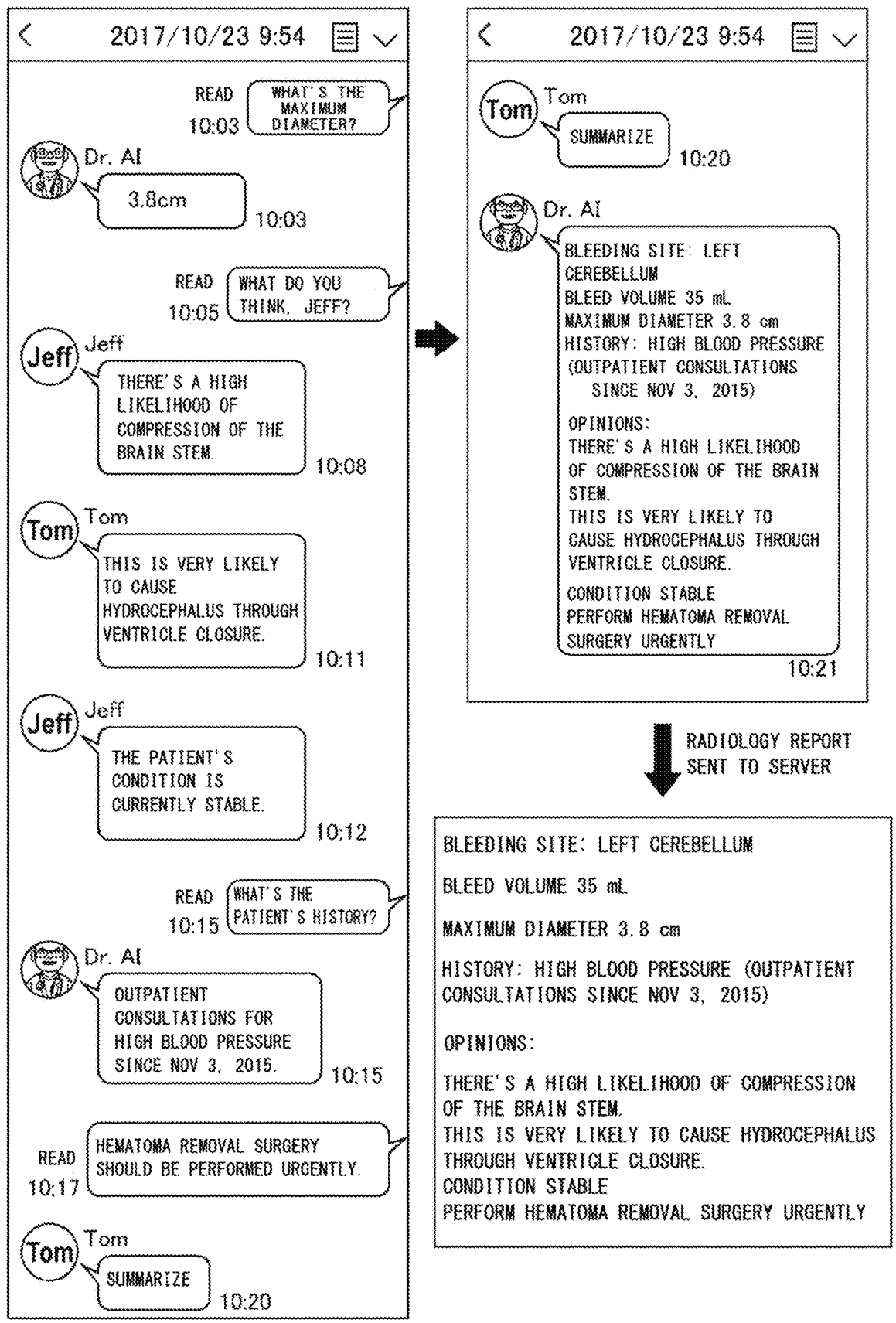
FIG. 6 shows an example of an exchange of messages in the virtual conference according to the first exemplary embodiment.

Now, a flow of processing of a virtual conference is described with reference to the flowchart in FIG. 4A to FIG. 4C and the examples of displays windows at the terminal device 30 in FIG. 5 and FIG. 6. Below, in order to distinguish posting of messages from a diagnostician and posting of messages from radiologists, the terminal devices 30 are described separately for the clinical department workstation 4 and the radiology workstations 3. Information generated by the information generation section 21 of the diagnostic support server 10 is described as messages from an AI doctor. When execution of the information generation section 21 is required, this is described as an enquiry to the AI doctor. The messages that are described include both texts and images.

When a scan image of a patient is imaged by one of the modalities 2 and a diagnostician sends the scan image from the clinical department workstation 4 to the diagnostic support server 10 (step ST1), the virtual conference creation section 15 creates a virtual conference and starts up a thread (step ST10). In order to invite, for example, the radiologists shown in FIG. 6 to the virtual conference, the diagnostician performs operations to enter participants in the virtual conference, for example, "Jeff" and "Tom", and invitation messages are sent from the invitation section 16 to the radiology workstations 3 (step ST11). The diagnostic support server 10 executes analysis of the scan image at the diagnostic object data analysis section 19 (step ST12).

When each radiologist sees the invitation message received by the participation section 37 of the radiology workstation 3 and accepts the invitation (step ST40), a notification of acceptance is sent from the participation section 37 to the diagnostic support server 10 (step ST41). When the invitation section 16 receives the notifications of acceptance from the radiology workstations 3, the invitation section 16 starts sending and receiving of messages in the virtual conference (step ST13). Messages posted to the virtual conference are recorded in order at the log recording section 18.

The diagnostic object data analysis section 19 obtains a line encircling a bleeding region and text information such as, for example, "35 mL bleed observed in the left cerebellum" by image analysis of the diagnostic object scan image posted to the virtual conference. As shown in FIG. 5, the diagnostic object data analysis section 19 posts the scan image, an image in which the line encircling the bleeding region is overlaid on the scan image, and a message of the text information to the virtual conference as messages from the AI doctor (step ST14). The radiology workstations 3 and clinical department workstation 4 display the message posted to the virtual conference at the diagnostic object data display section 38 (step ST2 and step ST42).

Then, the conference is conducted between the diagnostician and the radiologists. For example, as shown in FIG. 6, a message 1 is posted from the clinical department workstation 4 by the post message sending section 39 (step ST3); for example, "What's the maximum diameter?". When message 1 is posted, the message sending and receiving section 17 of the diagnostic support server 10 receives message 1 from the clinical department workstation 4 (step ST15), and sends the received message to each of the radiology workstations 3 of the radiologists Jeff and Tom (step ST16). Each radiology workstation 3 displays the message 1 received by the virtual conference display section 40 (step ST43). At the diagnostic support server 10, message 1 is analyzed by the message analysis section 20 (step ST17). From the results of analysis of message 1, the diagnostic support server 10 makes a determination that diagnosis is not ending (step ST18). The result of the determination in step ST18 is negative (No), and a determination is made that the message is about a measurement of the scan image and therefore is an enquiry to the AI doctor (step ST19). Because the result of the determination in step ST19 is affirmative (Yes), a message 2 presenting a measurement result of the bleeding location is generated from results obtained by the information generation section 21 performing image analysis (step ST20); for example, "3.8 cm." Message 2 is posted to the virtual conference by the related information sending section 22. The posted message 2 is sent from the message sending and receiving section 17 to the clinical department workstation 4 and the radiology workstations 3 (step ST21), and the radiology workstations 3 and clinical department workstation 4 each display the received message 2 at the related information display section 41 (step ST5 and step ST44). When this processing ends, the diagnostic support server 10 goes into a waiting state (a standby state) until the next post message is received (step ST22).

Subsequently, a message 3 is posted from the clinical department workstation 4 to the virtual conference by the post message sending section 39 (step ST3); for example, "What do you think, Jeff?" When message 3 is posted, the diagnostic support server 10 recovers from the waiting state in step ST15, receives message 3 from the clinical department workstation 4 at the message sending and receiving section 17 (step ST15), and sends the received message to the radiology workstations 3 (step ST16). At each of the radiology workstations 3 of the radiologists Jeff and Tom, the posted message 3 is displayed at the virtual conference display section 40 (step ST43). Message 3 is analyzed by the message analysis section 20 of the diagnostic support server 10 (step ST17), and a determination is made from the results of analysis of message 3 that the diagnosis is not ending (step ST18). Because the result of the determination in step ST18 is negative (No) and the name "Jeff", who is a participant, is included in message 3, a determination is made that message 3 is a message to a participant in the virtual conference (step ST19). Because the result of the determination in step ST19 is negative (No), processing to generate information is not executed by the information generation section 21, and the diagnostic support server 10 goes into the waiting state until the next post message is received (step ST22).

Figure 4B:
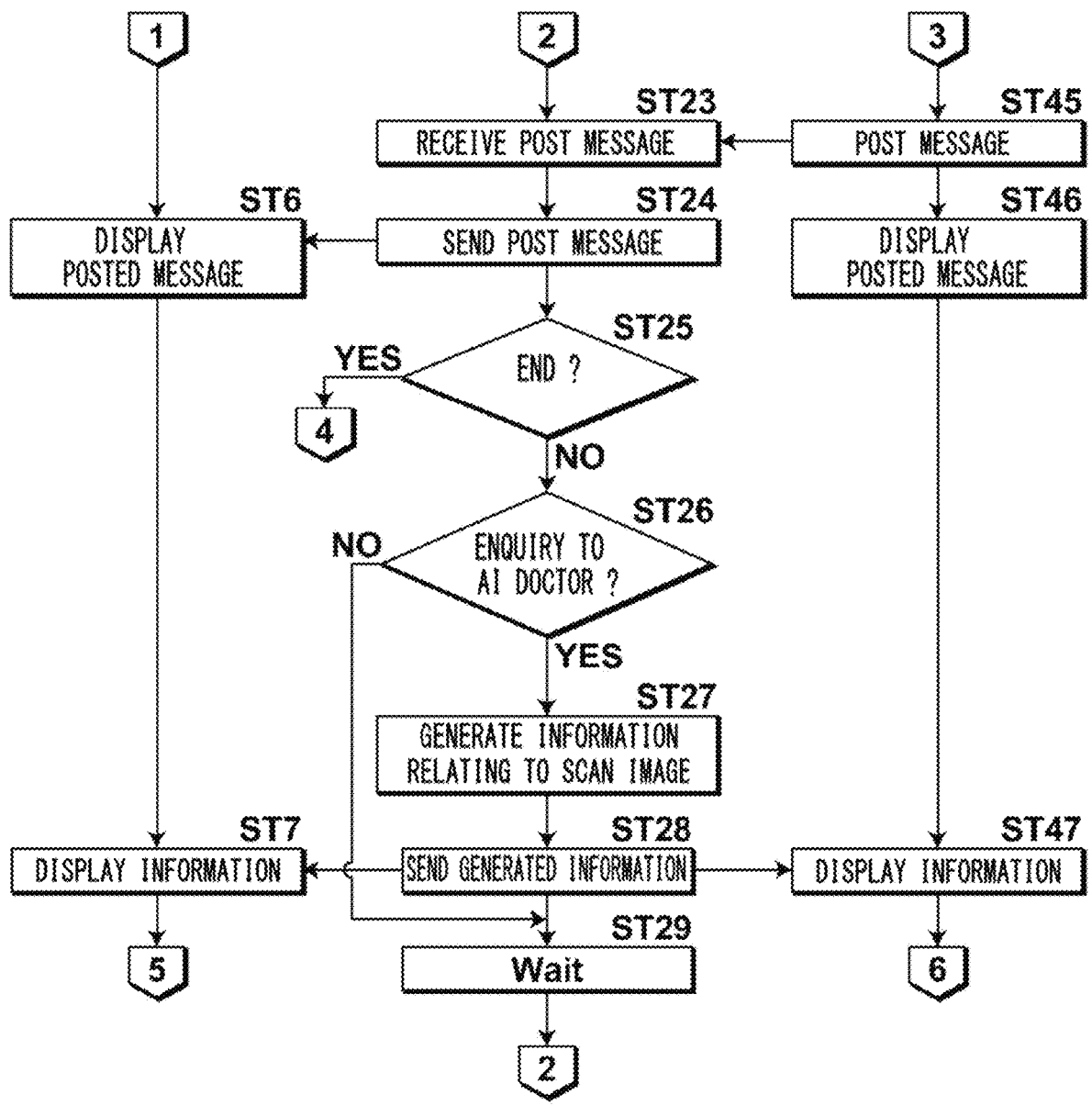
FIG. 4B is (part 2 of) the flowchart showing the flow of processing of the virtual conference according to the first exemplary embodiment of the present disclosure.

Now, a case in which a message is posted from the radiology workstations 3 is described in accordance with the flowchart of FIG. 4B. A message 4 is posted from the radiology workstation 3 of the radiologist Jeff by the post message sending section 39; for example, "There's a high likelihood of compression of the brain stem." When message 4 is posted (step ST45), the diagnostic support server 10 recovers from the waiting state in step ST23, the message sending and receiving section 17 receives message 4 from the radiology workstation 3 of the radiologist Jeff (step ST23), and the message sending and receiving section 17 sends the received message 4 to both the radiology workstation 3 of the radiologist Tom and the clinical department workstation 4 of the diagnostician (step ST24). In FIG. 4B, the posted message is sent only to the clinical department workstation 4, but the posted message is also sent to each radiology workstation 3 beside the radiology workstation 3 from which the message was posted. However, because the flow of processing is the same as at the clinical department workstation 4, this flow is omitted as appropriate in FIG. 4B. The message analysis section 20 of the diagnostic support server 10 analyzes message 4. From the results of analysis of the message, a determination is made that message 4 is not the end of diagnosis (step ST25). The result of the determination in step ST25 is negative (No), and a determination is made that message 4 is a message to a participant in the virtual conference (step ST26). The result of the determination in step ST26 is negative (No), and the information generation section 21 does not execute processing to generate information. In this state, the diagnostic support server 10 goes into the waiting state until the next post message is received (step ST29). Step ST27 and step ST28 are executed only when it is determined that a posted message is an enquiry to the AI doctor (when the result of the determination in step ST26 is affirmative). The generated information (step ST27) is sent to the radiology workstations 3 and the clinical department workstation 4 (step ST28), and the sent information is displayed at the radiology workstations 3 and the clinical department workstation 4 (step ST7 and step ST47).

As described above, messages posted by doctors participating in the virtual conference are repeatedly sent and received, the message analysis section 20 makes determinations as to whether posted messages are messages between the participants or enquiries to the AI doctor and, when a posted message is an enquiry to the AI doctor, the information generation section 21 generates information relating to the scan image and posts the information to the virtual conference.

Figure 4C:
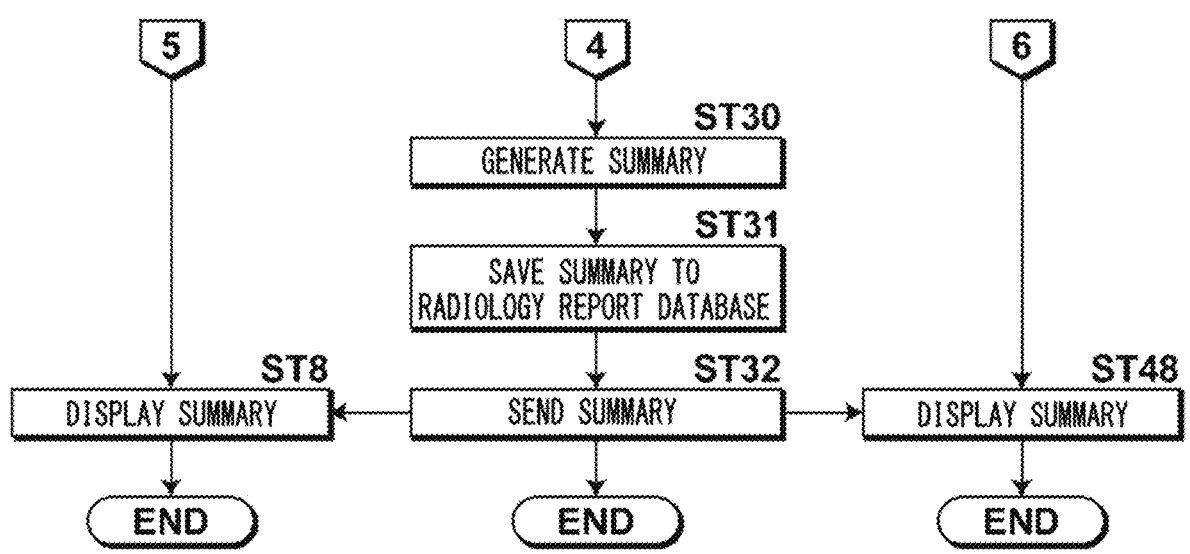
FIG. 4C is (part 3 of) the flowchart showing the flow of processing of the virtual conference according to the first exemplary embodiment of the present disclosure.

Finally, a case in which a report is generated in accordance with the flowchart in FIG. 4B and FIG. 4C is described. As shown in FIG. 6, a message 5 is posted from the post message sending section 39 of the radiology workstation 3 of the radiologist Tom (step ST45); for example, "Summarize". The message sending and receiving section 17 of the diagnostic support server 10 sends the message received from the radiology workstation 3 of the radiologist Tom to both the radiology workstation 3 of the radiologist Jeff and the clinical department workstation 4 (step ST24). The message analysis section 20 of the diagnostic support server 10 makes a determination that message 5 is a message indicating the end of diagnosis (step ST25). As shown by the flowchart in FIG. 4C, because the result of the determination in step ST25 is affirmative (Yes), in accordance with the results of analysis of message 5, the summary generation section 23 generates a summary from the messages recorded at the log recording section 18 (step ST30). The summary generation section 23 puts the summary and the scan image into the report format and stores this radiology report in the radiology report database 8 (step ST31). The summary is also posted to the virtual conference, and the posted summary is sent from the message sending and receiving section 17 to the clinical department workstation 4 and the radiology workstations 3 (step ST32). As shown at the upper right of FIG. 6, the summary is displayed at the clinical department workstation 4 and the radiology workstations 3 in the form of a message from the AI doctor (step ST8 and step ST48).

As is described in detail above, in the first exemplary embodiment, plural doctors may conduct a virtual conference while using the diagnostic support device to acquire various kinds of information relating to an examination image. Because AI functions are provided to the diagnostic support device, information obtained by using AI functions may be added to the doctors' information, and an accurate diagnosis may be made. In addition, because a function for summarizing messages posted to the virtual conference is provided, a radiology report may be created automatically.

Above, a case is described in which invitation messages are sent and then messages start to be sent to and received from users participating in the virtual conference. However, messages may start to be sent to and received from the registered users when the virtual conference is created.

Now, a second exemplary embodiment of the present disclosure is described. The present exemplary embodiment differs from the first exemplary embodiment in that the virtual conference is conducted at a single computer. Structures that are the same as in the first exemplary embodiment are assigned the same reference symbols and detailed descriptions thereof are not given here.

Figure 7:
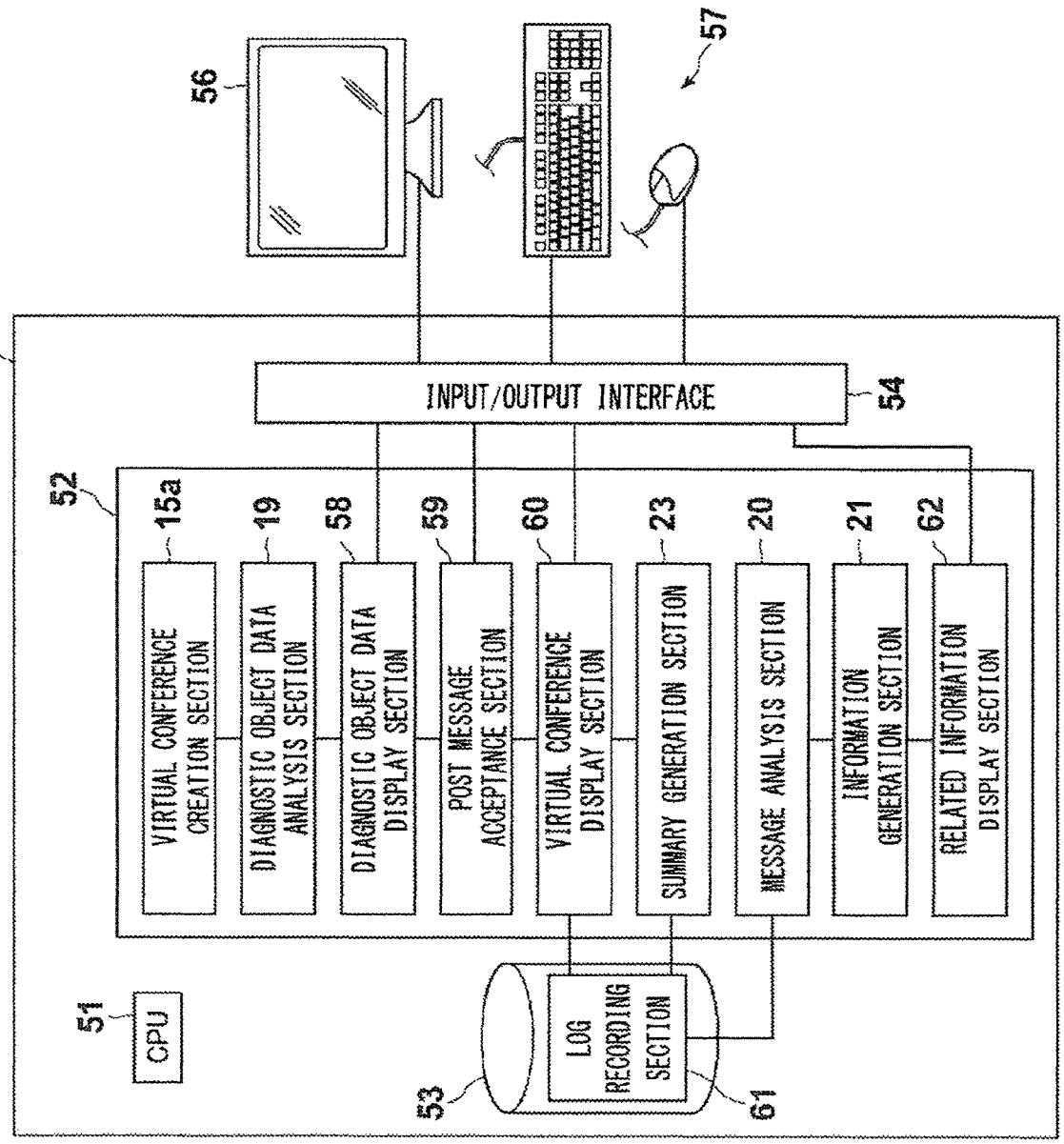
FIG. 7 is a diagram showing schematic structures of a diagnostic support device according to a second exemplary embodiment of the present disclosure.

As shown in FIG. 7, a diagnostic support device 50 according to the second exemplary embodiment is a computer equipped with widely known hardware structures such as a CPU 51, memory 52, storage 53, an input/output interface 54, a communications interface (not shown in the drawings), a data bus (not shown in the drawings) and the like. The diagnostic support device 50 is connected to a display 56 and an input device 57 such as a keyboard and mouse or the like. During operations of this computer, a diagnostic support program is stored in the memory 52, and the CPU 51 executes processing in accordance with the program stored in the memory 52. Thus, the computer functions as the diagnostic support device 50. As required, the computer may be provided with a GPU.

In the present exemplary embodiment, the diagnostic support program of the present disclosure is installed at the clinical department workstation 4 or one of the radiology workstations 3. Thus, the clinical department workstation 4 or radiology workstation 3 functions as the diagnostic support device 50 according to the present exemplary embodiment.

The CPU 51 executes the functions of respective sections of the diagnostic support device in accordance with the diagnostic support program. However, as an alternative to the CPU 51 that is a general purpose processor that executes software to function as various processing sections, a programmable logic device such as an FPGA or the like may be employed. Further, the processing of the respective sections may be executed by a dedicated electronic circuit or the like such as an ASIC or the like. This processing section may be structured by one of these various kinds of processors, or may be structured by combining two or more processors of the same or different kinds.

As shown in FIG. 7, the diagnostic support device 50 functions as a virtual conference creation section 15a, the diagnostic object data analysis section 19, a diagnostic object data display section 58, a post message acceptance section 59, a virtual conference display section 60, a log recording section 61, the message analysis section 20, the information generation section 21, a related information display section 62, and the summary generation section 23.

When diagnostic object data is received, the virtual conference creation section 15a automatically creates a virtual conference. The log recording section 61 is provided to store a log of messages posted in the virtual conference.

The log recording section 61 is a region in the storage 53 that is assigned to a corresponding virtual conference. The log recording section 61 records messages posted to the corresponding virtual conference in order of posting.

The diagnostic object data display section 58 posts the diagnostic object data to the virtual conference. The diagnostic object data display section 58 may display the diagnostic object data in a window of the virtual conference, but in a case in which the diagnostic object data is an image, the diagnostic object data display section 58 may display the diagnostic object image using a viewer. A case in which the diagnostic object data is a medical image for examining a disorder of a patient (below referred to as a scan image) is described as an example.

The post message acceptance section 59 accepts messages entered using the input device 57 to be posted to the virtual conference.

The virtual conference display section 60 displays messages posted to the virtual conference on the display 56 in order of posting. The posted messages are also recorded to the log recording section 61.

The related information display section 62 displays information relating to the scan image that is generated by the information generation section 21 on the display 56. The related information display section 62 may post the information relating to the scan image to the virtual conference and display the information in the window of a thread of the virtual conference. Alternatively, in a case in which the information relating to the scan image is an image, the image may be displayed at the display 56 using a separate viewer.

The diagnostic object data analysis section 19, the message analysis section 20 and the information generation section 21 are the same as in the first exemplary embodiment, and therefore are not described in detail here.

To perform image analysis of a scan image, the diagnostic support device 50 may be provided with a CNN that employs a deep learning technique to conduct learning, and the CNN may be used for image analysis at the diagnostic object data analysis section 19 and the information generation section 21. Alternatively, image analysis may be performed by a separately provided image processing server, and a CNN may be provided at the image processing server.

Figure 8:
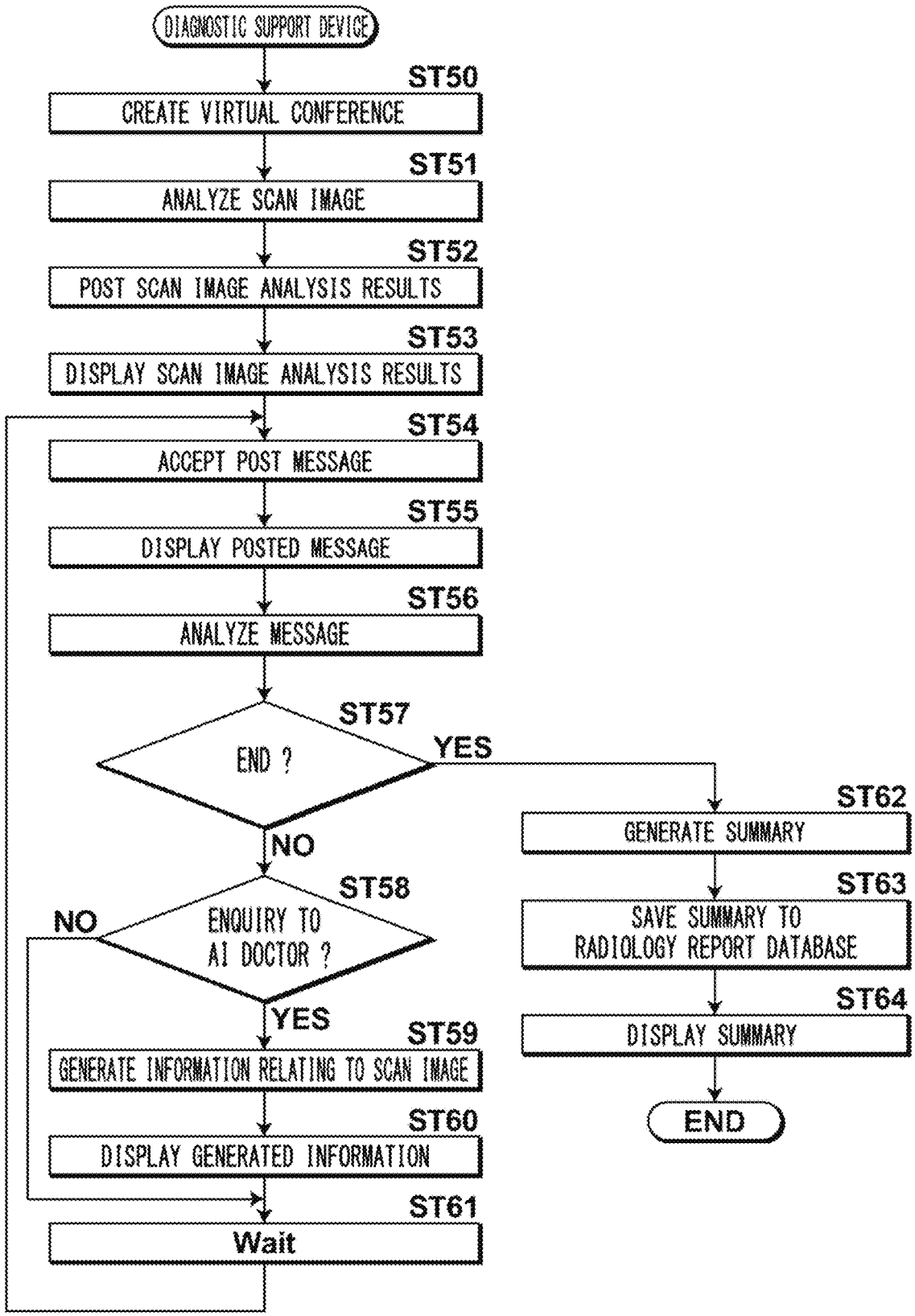
FIG. 8 is a flowchart showing a flow of processing of a virtual conference according to the second exemplary embodiment of the present disclosure.
Figure 9:
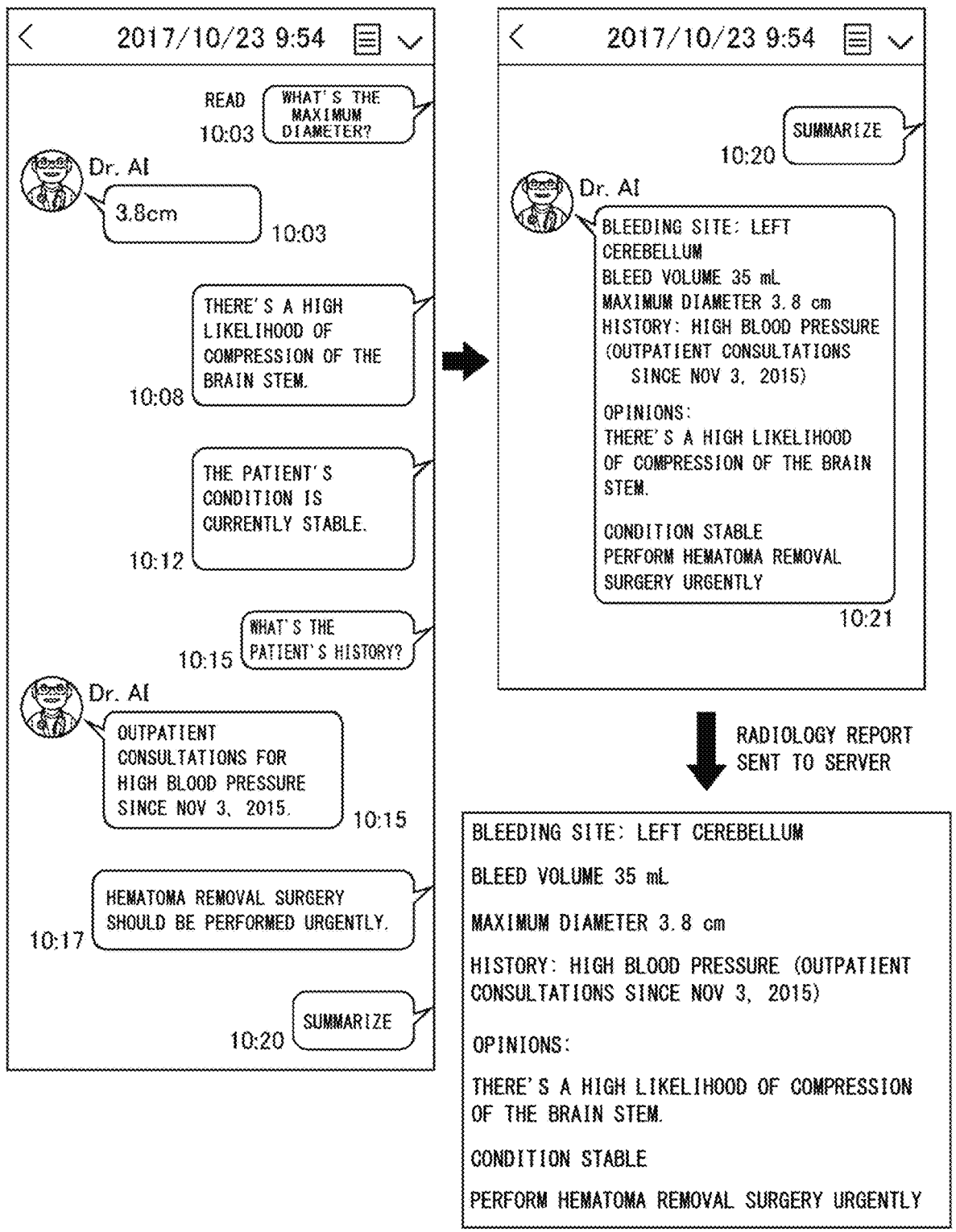
FIG. 9 shows an example of an exchange of messages in the virtual conference according to the second exemplary embodiment.

Now, a flow of processing of a virtual conference is described with reference to the flowchart in FIG. 8 and the examples of displays windows in FIG. 5 and FIG. 9. Information provided by the diagnostic support device 50 is described as messages from an AI doctor. When execution of the information generation section 21 is required, this is described as an enquiry to the AI doctor. The messages that are described include both texts and images.

When a scan image of a patient is imaged by one of the modalities 2 and the scan image is received at the clinical department workstation 4 (or one of the radiology workstations 3), the virtual conference creation section 15a creates a virtual conference (step ST50). The diagnostic object data analysis section 19 executes analysis of the scan image (step ST51).

The diagnostic object data analysis section 19 obtains a line encircling a bleeding region and text information such as, for example, "35 mL bleed observed in the left cerebellum" by the image analysis of the diagnostic object scan image posted to the virtual conference. As shown in FIG. 5, the diagnostic object data analysis section 19 posts the scan image, an image in which the line encircling the bleeding region is overlaid on the scan image, and a message of the text information to the virtual conference as a message from the AI doctor (step ST52). Messages posted to the virtual conference are recorded in order at the log recording section 18, and the messages posted to the virtual conference are displayed at the diagnostic object data display section 58 (step ST53).

Then, the conference is conducted by a doctor. For example, as shown in FIG. 9, a message 1 is posted through the post message acceptance section 59 (step ST54); for example, "What's the maximum diameter?", and message 1 is displayed at the virtual conference display section 60 (step ST55). The message analysis section 20 analyzes the posted message 1 (step ST56). From the results of analysis of message 1, the diagnostic support device 50 makes a determination that message 1 is not the end of diagnosis (No in step ST57). A determination is made that the message is about a measurement of the scan image and therefore is an enquiry to the AI doctor, (step ST58). Because the result of the determination in step ST58 is affirmative (Yes), a message 2 presenting a measurement result of the bleeding location is generated from results obtained by the information generation section 21 performing image analysis (step ST59); for example, "3.8 cm." The generated message 2 is posted to the virtual conference by the related information display section 62, and the posted message 2 is displayed at the virtual conference display section 60 (step ST60). The diagnostic support device 50 then goes into the waiting state until the next post message is accepted (step ST61). When the next message is received, the diagnostic support device 50 returns to step ST54.

Subsequently, a message 6 is posted through the post message acceptance section 59; for example, "There's a high likelihood of compression of the brain stem." When message 6 is accepted (step ST54), message 6 is displayed at the virtual conference display section 60 (step ST55). The message analysis section 20 analyzes the posted message 6 (step ST56). From the results of analysis of message 6, a determination is made that message 6 is not the end of diagnosis (step ST57). Because the result of the determination in step ST57 is negative (No), a determination is then made that message 6 is not an enquiry to the AI doctor (step ST58). The result of the determination in step ST58 is negative (No), and the diagnostic support device 50 goes into the waiting state until the next post message is received (step ST61).

As described above, the message analysis section 20 makes determinations as to whether messages posted by the doctor to the virtual conference are enquiries to the AI doctor and, when a posted message is an enquiry to the AI doctor, the information generation section 21 generates information relating to the scan image and posts the information to the virtual conference. By repeating this, a conference is conducted between the doctor and the AI doctor.

Finally, a message 5 is posted through the post message acceptance section 59 (step ST54); for example, "Summarize". The message analysis section 20 makes a determination that message 5 is a message indicating the end of diagnosis (step ST57). Because the result of the determination in step ST57 is affirmative (Yes), in accordance with the results of analysis of message 5, the summary generation section 23 generates a summary from the messages recorded at the log recording section 61 (step ST62). The summary generation section 23 puts the summary and the scan image into the report format and stores this radiology report in the radiology report database 8 (step ST63). The summary is also posted to the virtual conference, and the posted summary is displayed at the virtual conference display section 60 (step ST64).

As is described in detail above, in the second exemplary embodiment, a single doctor may conduct a virtual conference, using the diagnostic support device to acquire various kinds of information relating to an examination image. Because the diagnostic support device is provided with AI functions, AI information is added to the thoughts of the single doctor, and an accurate diagnosis may be made. In addition, because a function for summarizing messages posted to the virtual conference is provided, a radiology report may be created automatically.

What is claimed is:

1. A diagnostic support server device comprising:
a communication interface; and
a processor coupled to the communication interface and configured at least to:
receive, from the communication interface, a message posted to a virtual conference from a terminal device of a user participating in the virtual conference and send, through the communication interface, the posted message to another terminal device beside the terminal device of the user, the virtual conference being created in relation to diagnostic object data;
generate information relating to the diagnostic object data, the information being obtained in accordance with an analysis result of analyzing the posted message;
send, through the communication interface, the information relating to the diagnostic object data to the terminal device of the user and the another terminal device;
request for an assessment from the artificial intelligence (AI) doctor related to the diagnostic object data and receive from the AI doctor the assessment which is displayed on a chatting user interface associated with the virtual conference;
detect a posted message associated with the virtual conference that indicates a generation of a summary;
generates the summary automatically in response to having detected from the posted message which indicates the generation of the summary; and
conclude the virtual conference in response to generating the summary.

2. The diagnostic support server device according to claim 1, wherein the summary includes diagnosis information of the diagnostic object data.

3. The diagnostic support server device according to claim 2, wherein the processor is further configured to associate the summary with the diagnostic object data and stores the summary and diagnostic object data at a storage section.

4. The diagnostic support server device according to claim 1, wherein the processor is further configured to generate the summary in response to detecting a keyword which indicates an end of diagnosis of the diagnostic object data in the virtual conference is detected.

5. The diagnostic support server device according to claim 4, wherein the summary includes an assessment from the user participating in the virtual conference and an assessment from an artificial intelligence (AI) doctor.

6. The diagnostic support server device according to claim 1, wherein the information relating to the diagnostic object data includes at least one of
an image in which image processing is applied to an image of the diagnostic object data,
information that specifies a position of interest in an image of the diagnostic object data,
an image in which a mark is applied to a position of interest in the image of the diagnostic object data,
an image in which a position of interest in an image of the diagnostic object data is magnified,
an image that is retrieved in relation to the diagnostic object data,
information that specifies a slice position of a sectional image of the diagnostic object data,
an image in which a density gradation of an image of the diagnostic object data is adjusted, and information that associates the posted message with an image that is an object.

7. The diagnostic support server device according to claim 1, wherein the information relating to the diagnostic object data is a key image used for a diagnosis of the diagnostic object data.

8. The diagnostic support server device according to claim 7, wherein the processor is further configured to associate the key image with the summary and store the key image and summary at a storage section.

9. The diagnostic support server device according to claim 1, wherein the processor is further configured to automatically generate the virtual conference in response to receiving a scanned image related to the diagnostic object data.

10. A diagnostic support system comprising a diagnostic support server device and a plurality of terminal devices, the diagnostic support server device including:
   a communication interface; and
   a processor coupled to the communication interface and configured at least to:
   receive, from the communication interface, a message posted to a virtual conference from the terminal device of a user participating in the virtual conference and send, through the communication interface, the posted message to another of the terminal devices beside the terminal device of the user, the virtual conference being created in relation to diagnostic object data;
   generate information relating to the diagnostic object data, the information being obtained in accordance with an analysis result of analyzing the posted message;
   send, through the communication interface, the information relating to the diagnostic object data to the terminal device of the user and the another terminal device;
   request for an assessment from the artificial intelligence (AI) doctor related to the diagnostic object data and receive from the AI doctor the assessment which is displayed on a chatting user interface associated with the virtual conference;
   detect a posted message associated with the virtual conference that indicates a generation of a summary;
   generates the summary automatically in response to having detected from the posted message which indicates the generation of the summary; and
   conclude the virtual conference in response to generating the summary, and each terminal device including:
   a diagnostic object data display section that displays the diagnostic object data;
   a post message sending section that sends a message to be posted to the virtual conference to the diagnostic support server device;
   a virtual conference display section that displays the posted message in order of posting to the virtual conference; and
   a related information display section that displays the information relating to the diagnostic object data.

11. A diagnostic support process of a diagnostic support system including a diagnostic support server device and a terminal device, the diagnostic support process comprising:
   a message sending and receiving step of the diagnostic support server device receiving a message posted to a virtual conference from the terminal device of a user participating in the virtual conference and sending the posted message to another terminal device beside the terminal device, the virtual conference being created in relation to diagnostic object data;
   an information generation step of the diagnostic support server device generating information relating to the diagnostic object data, the information being obtained in accordance with an analysis result of analyzing the posted message;
   a related information sending step of the diagnostic support server device sending the information relating to the diagnostic object data to the terminal device and the another terminal device;
   a requesting step of requesting for an assessment from the artificial intelligence (AI) doctor related to the diagnostic object data and receive from the AI doctor the assessment which is displayed on a chatting user interface associated with the virtual conference;
   a detecting step of the diagnostic support server device detecting a posted message associated with the virtual conference that indicates a generation of a summary;
   a generating step of the diagnostic support server device generating the summary automatically in response to having detected from the posted message which indicates the generation of the summary; and
   a concluding step of the diagnostic support server device concluding the virtual conference in response to generating the summary,
   a diagnostic object data display step of the terminal device displaying the diagnostic object data;
   a post message sending step of the terminal device sending a message to be posted to the virtual conference to the diagnostic support server device;
   a virtual conference display step of the terminal device displaying the posted message in order of posting to the virtual conference; and
   a related information display step of the terminal device displaying the information relating to the diagnostic object data.

12. A non-transitory computer-readable recording medium storing therein a diagnostic support program that causes a computer to execute processing comprising:
   a message sending and receiving step of receiving a message posted to a virtual conference from a terminal device of a user participating in the virtual conference and sending the posted message to another terminal device beside the terminal device of the user, the virtual conference being created in relation to diagnostic object data;
   an information generation step of generating information relating to the diagnostic object data, the information being obtained in accordance with an analysis result of analyzing the posted message;
   a related information sending step of sending the information relating to the diagnostic object data to the terminal device of the user and the another terminal device;
   a requesting step of requesting for an assessment from the artificial intelligence (AI) doctor related to the diagnostic object data and receive from the AI doctor the assessment which is displayed on a chatting user interface associated with the virtual conference;
   a detecting step of detecting a posted message associated with the virtual conference that indicates a generation of a summary;
   a generating step of generating the summary automatically in response to having detected from the posted message which indicates the generation of the summary; and
   a concluding step of concluding the virtual conference in response to generating the summary.

13. A diagnostic support device comprising:
   a display panel; and a processor coupled to the display panel and configured at least to:
control the display panel to display diagnostic object data;
accept an entry of a message to be posted to a virtual conference, the virtual conference being created in relation to the diagnostic object data;
control the display panel to display the posted message in order of posting to the virtual conference;
generate information relating to the diagnostic object data, the information being obtained in accordance with an analysis result of analyzing the posted message;
control the display panel to display the information relating to the diagnostic object data;
request for an assessment from the artificial intelligence (AI) doctor related to the diagnostic object data and receive from the AI doctor the assessment which is displayed on a chatting user interface associated with the virtual conference;
detect a posted message associated with the virtual conference that indicates a generation of a summary;
generates the summary automatically in response to having detected from the posted message which indicates the generation of the summary; and
conclude the virtual conference in response to generating the summary.

14. A diagnostic support process at a diagnostic support device, the process comprising:
a diagnostic object data display step of displaying diagnostic object data;
a post message acceptance step of accepting entry of a message to be posted to a virtual conference, the virtual conference being created in relation to the diagnostic object data;
a virtual conference display step of displaying the posted message in order of posting to the virtual conference;
an information generation step of generating information relating to the diagnostic object data, the information being obtained in accordance with an analysis result of analyzing the posted message;
a related information display step of displaying the information relating to the diagnostic object data;
a requesting step of requesting for an assessment from the artificial intelligence (AI) doctor related to the diagnostic object data and receive from the AI doctor the assessment which is displayed on a chatting user interface associated with the virtual conference;
a detecting step of detecting a posted message associated with the virtual conference that indicates a generation of a summary;
a generating step of generating the summary automatically in response to having detected from the posted message which indicates the generation of the summary; and
a concluding step of concluding the virtual conference in response to generating the summary.

15. A non-transitory computer-readable recording medium storing therein a diagnostic support program that causes a computer to execute processing comprising:
a diagnostic object data display step of displaying diagnostic object data;
a post message acceptance step of accepting entry of a message to be posted to a virtual conference, the virtual conference being created in relation to the diagnostic object data;
a virtual conference display step of displaying the posted message in order of posting to the virtual conference;
an information generation step of generating information relating to the diagnostic object data, the information being obtained in accordance with an analysis result of analyzing the posted message;
a related information display step of displaying the information relating to the diagnostic object data;
a requesting step of requesting for an assessment from the artificial intelligence (AI) doctor related to the diagnostic object data and receive from the AI doctor the assessment which is displayed on a chatting user interface associated with the virtual conference;
a detecting step of detecting a posted message associated with the virtual conference that indicates a generation of a summary;
a generating step of generating the summary automatically in response to having detected from the posted message which indicates the generation of the summary; and
a concluding step of concluding the virtual conference in response to generating the summary.

* * * * *